United States Patent [19]

Lang et al.

[11] 4,411,502
[45] Oct. 25, 1983

[54] OPHTHALMOLOGICAL INSTRUMENT FOR EXAMINATION OF ANTERIOR AND POSTERIOR PORTIONS OF THE EYE

[75] Inventors: Walter H. Lang; Franz Muchel, both of Konigsbronn; Kurt Schulz; Gunther Summerer, both of Oberkochen, all of Fed. Rep. of Germany

[73] Assignee: Carl Zeiss-Stiftung, Oberkochen, Fed. Rep. of Germany

[21] Appl. No.: 206,066

[22] Filed: Nov. 12, 1980

[30] Foreign Application Priority Data

Nov. 13, 1979 [DE] Fed. Rep. of Germany ....... 2945744

[51] Int. Cl.³ ............................................. A61B 3/14
[52] U.S. Cl. .................................... 351/206; 351/214; 351/221
[58] Field of Search ..................... 351/7, 14, 206, 214, 351/221

[56] References Cited

U.S. PATENT DOCUMENTS 3,944,342 3/1976 Martinez ............................... 351/14

*Primary Examiner*—F. L. Evans
*Attorney, Agent, or Firm*—Hopgood, Calimafde, Kalil, Blaustein & Judlowe

[57] ABSTRACT

The invention contemplates an improved ophthalmological instrument wherein photo slit-lamp function (for anterior-chamber examination of an eye) are combined with fundus-camera functions (for posterior-chamber examination of the eye), with important advantages of manipulating convenience and reduced cost. The invention is disclosed (a) for the case of a photo slit-lamp accessory for use with an existing fundus camera and (b) for the case of a more compact new instrument to serve both functions.

6 Claims, 3 Drawing Figures

OPHTHALMOLOGICAL INSTRUMENT FOR EXAMINATION OF ANTERIOR AND POSTERIOR PORTIONS OF THE EYE

BACKGROUND OF THE INVENTION

The present invention relates to an ophthalmological instrument for examination of the eye.

In ophthalmological diagnosis, the examination of anterior portions of the eye (cornea, anterior chamber, lens) and that of the posterior portions of the eye (vitreous body, retina) have been carried out separately from each other. A photo slit-lamp is used for examining and photographing anterior portions of the eye, while a fundus camera is used for examination of posterior portions of the eye. The two instruments are costly and expensive, even from a consideration of the optical equipment alone. Since examinations of the anterior and posterior portions of the eye are separately performed, the two instruments are even frequently set up and used in locations spaced apart, in which case each instrument requires a separate power pack, an instrument table with corresponding headrest, a miniature camera with motorized film drive, and a device for the marking of the time of examination and the patient number. Such apparatus expense is considered a disadvantage by many users.

BRIEF STATEMENT OF THE INVENTION

The object of the present invention is to reduce the cost of apparatus for examination of anterior and posterior portions of the eye.

This object is achieved in accordance with the invention by combining photo-slit lamp illumination and a fundus camera to form a single instrument for examination and photography of anterior and posterior portions of the eye. Stereoscopic viewing for the fundus camera is advantageously provided in such a combined instrument.

One advantageous embodiment of the combination instrument of the invention is characterized by the fact that the photo-slit lamp illumination group is coupled mechanically with the fundus camera and that the photo-slit lamp illumination group and the fundus camera are swingable jointly and individually about an axis of rotation, the angle between the optical axis of the fundus camera and the optical axis of the slit lamp being variable. With such an instrument combination, an existing fundus camera can be converted at relatively little expense into a photo-slit lamp fundus camera.

Should an examining office need to be re-equipped, the photo slit-lamp fundus camera can be designed as a compact instrument which is characterized by the fact that the illumination group of the fundus camera serves for slit illumination and slit imaging, the illumination group and the observation part of the fundus camera being swingable jointly and severally around an axis of rotation.

The particular advantages obtained by the invention are that apparatus expense for eye-examination equipment can be considerably decreased, that the space required by the ophthalmologist for examining instrumentation is reduced, and that an existing fundus camera may be upgraded at little expense into a high-quality photo-slit lamp fundus camera.

DETAILED DESCRIPTION

Illustrative embodiments of the invention are shown in the accompanying drawings and will be described in further detail. In said drawings.

Figure 1:
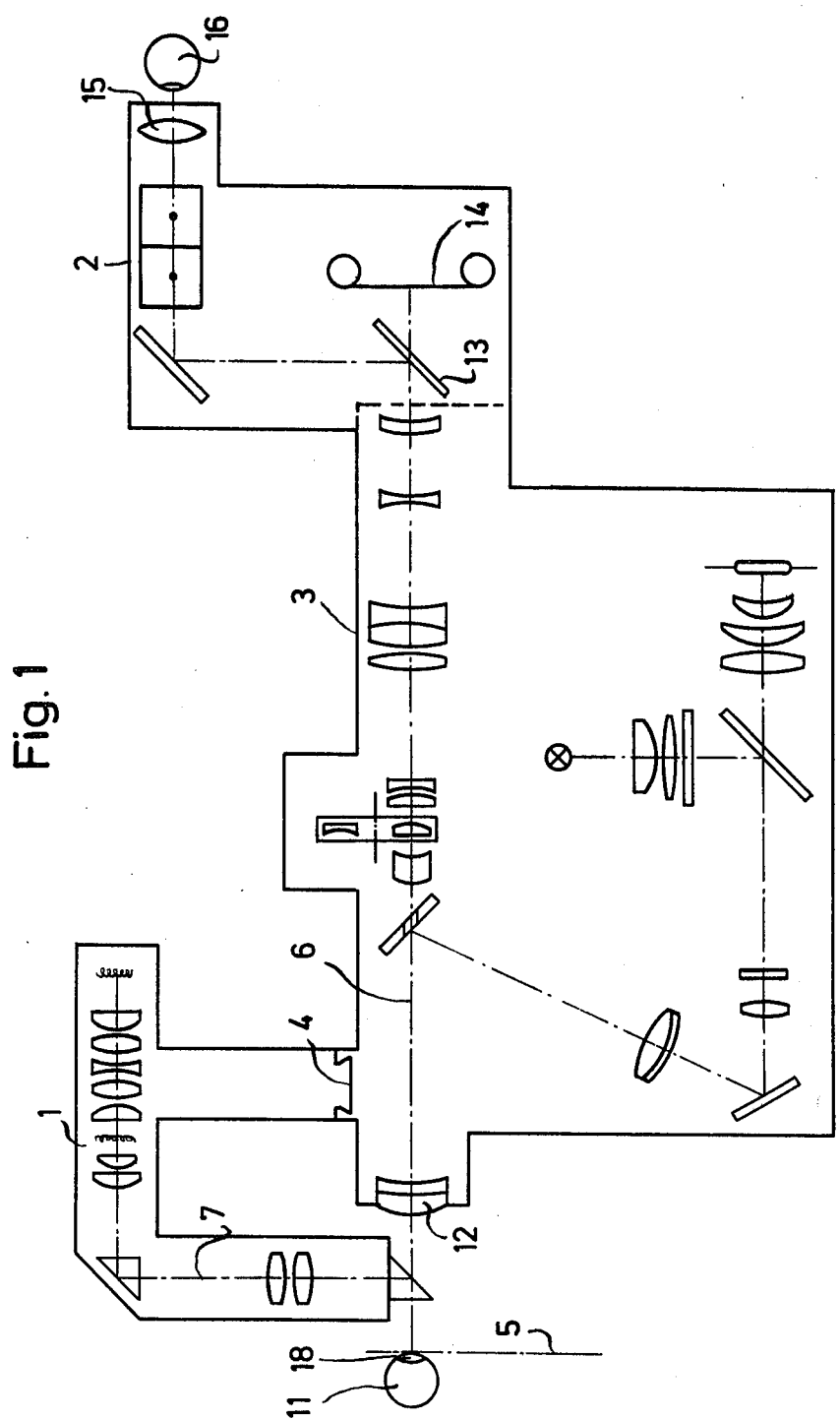
FIG. 1 is a diagrammatic sectional view of a first instrument which illustrates a fundus camera with which a photo slit-lamp illuminating group has been combined.

In FIG. 1, reference numeral 1 designates the the illumination group of a photo-slit lamp such as described, for instance, in Prospectus 30241-d/Ma III/74 Noo of the Carl Zeiss Company. And numerals 2 and 3 designate components of a known fundus camera, as for example that known from Carl Zeiss Prospectus 30-245.1-d/MA X/77 Koo, or from German published application 2,741,992 (Offenlegungschrift), the illumination group and the observation group being combined as the component unit 3, and the ocular head being the other component unit 2. The photo slit-lamp illumination group 1 is shown selectively and mechanically coupled with the fundus camera 2–3, via a connecting part 4. This coupling is such as to provide an axial offset of the fundus camera away from the eye 11 of the patient, whereby the objective 12 of the fundus camera is focused on anterior portions of the eye. In the ocular head 2 of the fundus camera, a reflecting mirror 13 is provided to deflect the observation ray path either onto a documentation device 14 or else, via a binocular observation device 15, towards the observer 16. The photo slit-lamp illumination group 1 and the fundus camera 2–3 are jointly or individually swingable about an axis of rotation 5; and a reflecting prism forming part of the slit-lamp unit folds the slit-lamp optical axis at intercept with the radial plane swept by the fundus-camera axis, when unit 3 is adjusted about axis 5.

Figure 2:
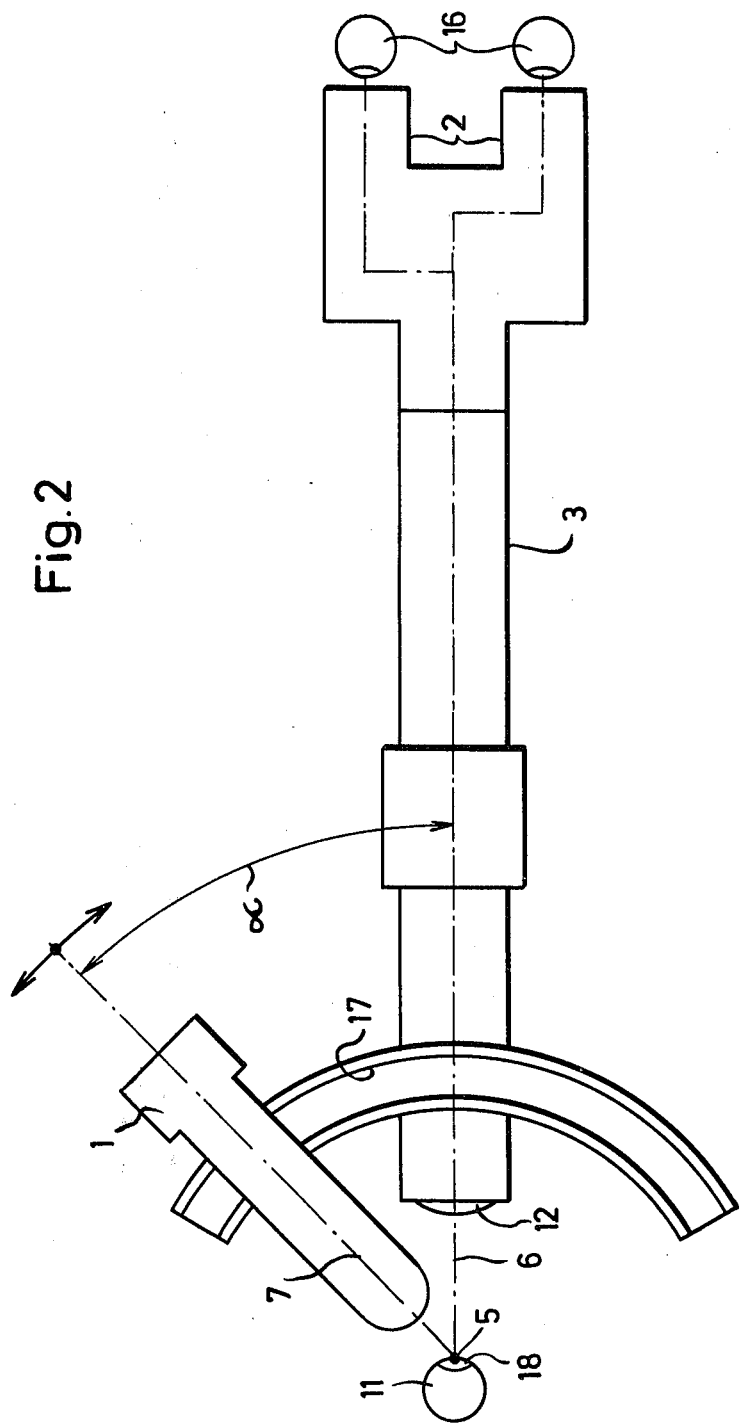
FIG. 2 is a plan view of the instrument shown in FIG. 1.

The plan view of FIG. 2 shows an arcuate track 17 on which the slit-lamp illumination group 1 is guided for examination of anterior portions 18 of the eye. The adjustment angle α can thus be set as desired.

Figure 3:
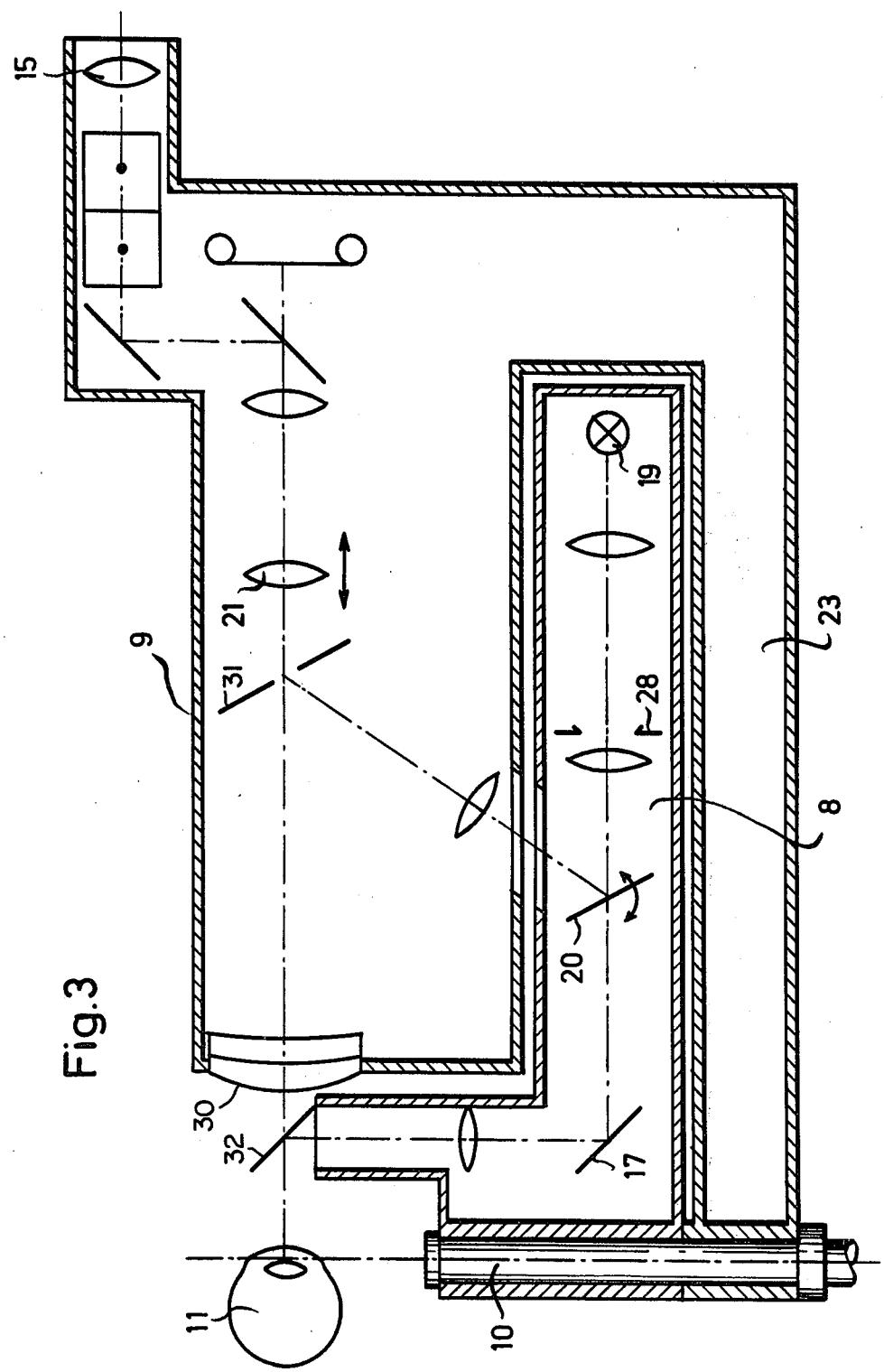
FIG. 3 is a diagrammatic sectional view of a second combination and more compact combination instrument in which slit-lamp illumination is integrated into the illumination of a fundus camera.

In the embodiment shown in FIG. 3, the observation part of the fundus camera (including an objective 30 and a focusing lens 21) and an apertured mirror part 31 part of the illumination group are arranged in a first component unit 9; unit 9 is connected via a support-arm part 23 for angular displacement about a shaft 10. A second component unit 8 contains that portion of the illumination group of the fundus camera which is also used for slit illumination; unit 8 is also connected for angular displacement about shaft 10. In a photo-slit lamp usage, the slit is arranged at a diaphragm location 28, being illuminated by a lamp 19 and focused via the illumination optical system of unit 8 (via a partially reflecting folding mirror 32) onto the anterior portions of the eye. In this case, the mirror 20 is swung out of the ray path (as suggested by a double-headed arcuate arrow), or it may be temporarily inserted at the location of folding mirror 17.

When using the combination instrument as a fundus camera, the mirror 20 remains in place. A double-headed straight arrow suggests that lens 21 of unit 9 can be shifted axially in order to focus the observation optical system on posterior portions of the eye. The optical groups of units 9 and 8 are swingable jointly and individually about shaft 10.

The embodiment shown by way of example in FIGS. 1 and 2 (namely, the combination of an existing fundus camera with a slit-lamp illumination group) is not limited to the standing arrangement shown, since such a combination will also be seen to be achievable with suspended instrument groups. The essential point is that a mechanical connection be produced between the slit-lamp illumination group and the fundus camera and that both of the combined component parts are swingable jointly and individually around the same axis of rotation.

What is claimed is:

1. An ophthalmological instrument having selective capability for examining anterior and posterior portions of the eye, comprising a fundus-camera optical system, a slit-lamp optical system, and means mounting both said systems for independent and selective displacement about a single axis of rotation, said fundus-camera optical system having a first optical axis normal to said axis of rotation and including an objective and other optical elements at radial offset from said axis of rotation, said slit-lamp optical system having a light source and optical elements on a second optical axis normal to said axis of rotation and at axial offset from the geometrical plane swept by said first optical axis upon fundus-camera system displacement about said axis of rotation, first mirror elements forming part of said slit-lamp optical system and folding said second optical axis into said geometrical plane and within said radial offset, the mirror element at said geometrical plane being partially reflecting and being forward of the objective, whereby said fundus-camera system may be operative when both said systems are in a single geometrical plane which includes said axis of rotation, and second mirror elements for folding light from said source from said second optical axis to said first optical axis when said first and second optical axes are in said single geometric plane which includes said single axis of rotation, said second mirror elements including (i) a fixed partially reflecting mirror on said first optical axis and behind said objective and (ii) a movable mirror on said second optical axis, said movable mirror being selectively movable into and out of folding relation with light from said source.

2. An ophthalmological instrument having selective capability for examining anterior and posterior portions of the eye, comprising first and second housings and means mounting both said housings for independent and selective displacement about a single axis of rotation, a fundus camera including an optical system having first components in said first housing and on a first optical axis normal to said axis of rotation and including an objective at radial offset from said axis of rotation, said fundus camera including an illumination group in said second housing and mirror means folding light from said illumination group onto said first optical axis at a location behind said objective when said housings are at the same angular location about said axis of rotation, slit-lamp optical components in said second housing, and selectively operable means within said second housing for directing light from said illumination group to serve said slit-lamp optical components or said fundus camera as desired, said slit-lamp optical components including mirror means forward of the fundus-camera objective and folding the axis of said slit-lamp optical components to the geometrical plane swept by said first optical axis by reason of first-housing displacement about said axis of rotation.

3. The instrument of claim 2, in which said illumination group of said fundus camera includes a diaphragm, and in which a slit is arranged at the diaphragm location at least when said selectively operable means is operated to select a slit-lamp illumination of an eye.

4. The instrument of claim 2, in which said first components on said first optical axis include a focusing-lens element at a location behind the location of illumination-group folding into said first optical axis.

5. In an ophthalmological instrument having selective capability for examining anterior and posterior portions of the eye, wherein fundus-camera optical components and slit-lamp optical components are independently angularly positionable in spaced planes normal to a single axis of rotation, said fundus-camera optical components including an objective on a fundus-camera axis normal to and at radial offset from said axis of rotation, and said slit-lamp optical components including means folding the axis of said slit-lamp optical components into the geometrical plane swept by said fundus-camera axis in the course of displacement about said axis of rotation, the improvement in which a fundus-camera illumination group is carried with said slit-lamp optical components for angular displacement therewith and in which said fundus-camera optical components include reflecting means folding light from said illumination group into said fundus-camera axis when said fundus-camera optical components and said slit-lamp components are at the same angular location about said axis of rotation, and selectively operable means including a movable mirror and having a first position directing light from said illumination group onto said fundus-camera axis and a second position directing light from said illumination group onto the axis of said slit-lamp components, said movable mirror being located between said illumination group and said first-mentioned folding means.

6. The instrument of claim 5, in which said illumination group includes a diaphragm and means for arranging a slit at the diaphragm location.

* * * * *